US012142169B2

(12) United States Patent
Golarz et al.

(10) Patent No.: US 12,142,169 B2
(45) Date of Patent: Nov. 12, 2024

(54) PRE-OPERATIVE ASSESSMENT TOOL AND METHOD FOR PREDICTING DIFFICULT AIRWAY

(71) Applicants: Bernadette Golarz, Berwyn, PA (US); Amanda Dillon Rios, Philadelphia, PA (US)

(72) Inventors: Bernadette Golarz, Berwyn, PA (US); Amanda Dillon Rios, Philadelphia, PA (US)

( * ) Notice: Subject to any disclaimer, the term of this patent is extended or adjusted under 35 U.S.C. 154(b) by 427 days.

(21) Appl. No.: 17/701,117

(22) Filed: Mar. 22, 2022

(65) Prior Publication Data
US 2022/0301460 A1 Sep. 22, 2022

Related U.S. Application Data

(60) Provisional application No. 63/164,182, filed on Mar. 22, 2021.

(51) Int. Cl.
*A61B 5/107* (2006.01)
*G09B 29/00* (2006.01)
*G09F 7/00* (2006.01)

(52) U.S. Cl.
CPC .............. *G09F 7/00* (2013.01); *A61B 5/1072* (2013.01); *G09B 29/00* (2013.01)

(58) Field of Classification Search
CPC ........ A61B 5/107; A61B 5/1072; A61B 5/103
USPC ............................... 33/494, 511, 512, 679.1
See application file for complete search history.

(56) References Cited

U.S. PATENT DOCUMENTS

| | | | | | |
|---|---|---|---|---|---|
| 1,976,045 | A | * | 10/1934 | Sorenson | A61C 19/00 33/513 |
| 3,377,712 | A | * | 4/1968 | Farkas | A61B 5/107 33/512 |
| 4,843,720 | A | * | 7/1989 | Kim | G01B 3/20 33/513 |
| 5,156,161 | A | * | 10/1992 | Lollar | A61B 5/0053 606/205 |

(Continued)

OTHER PUBLICATIONS

"Airway Assessment Cue-Card," Openairway.org. https://openairway.org/airway-assessment-cue-card/ [Date accessed: Oct. 23, 2020].

(Continued)

*Primary Examiner* — George B Bennett
(74) *Attorney, Agent, or Firm* — Bold IP PLLC; Binita Singh

(57) ABSTRACT

A pre-operative system and method are provided for predicting a difficult airway for intubation or mask ventilation in making a more accurate and confident prediction on difficult airway. The system may be provided as a two-sided card wherein a first side of the card may include a combination of predictive tests that are shown to be the most helpful in predicting a difficult airway. A ruler is also provided on an edge of the card to assist with measurements, along with an inch to centimeter conversion factor. A second side of the card includes a list of contributing factors for a difficult airway and clinical assessments findings associated with difficult mask ventilation. This cognitive aid may also comprise of a method to use the combination of predictive tests and contributing factors in conducting a thorough and confident assessment of an airway prior to a surgical procedure requiring anesthesia.

18 Claims, 3 Drawing Sheets

(56) References Cited

U.S. PATENT DOCUMENTS

| | | | | |
|---|---|---|---|---|
| 5,584,125 A * | 12/1996 | Prete | ............. | A61M 16/06 |
| | | | | 33/501.45 |
| 5,741,212 A * | 4/1998 | Matthews | ............. | A61B 5/444 |
| | | | | 600/300 |
| 6,341,429 B1 * | 1/2002 | Herskovitz | ............. | A61B 5/444 |
| | | | | 33/1 BB |
| 6,564,464 B1 * | 5/2003 | Keating | ............. | A61B 5/1071 |
| | | | | 33/512 |
| 6,843,769 B1 * | 1/2005 | Gandarias | ............. | A61B 1/0676 |
| | | | | 600/188 |
| 7,127,826 B2 * | 10/2006 | Russell | ............. | A61B 90/39 |
| | | | | 33/566 |
| 7,144,251 B1 * | 12/2006 | Karapetyan | ............. | A61C 19/04 |
| | | | | 33/513 |
| 7,628,215 B2 * | 12/2009 | Nickle | ............. | A01L 11/00 |
| | | | | 33/511 |
| 7,665,220 B1 * | 2/2010 | Gee | ............. | G01B 3/10 |
| | | | | 33/511 |
| 8,127,459 B2 | 3/2012 | Nunes et al. | | |
| 8,170,888 B2 | 5/2012 | Silverman | | |
| 8,276,287 B2 * | 10/2012 | Estocado | ............. | A61B 5/444 |
| | | | | 33/1 BB |
| 8,460,215 B2 | 6/2013 | Connor et al. | | |
| 8,739,444 B2 * | 6/2014 | Poole | ............. | G01B 3/34 |
| | | | | 283/81 |
| 8,936,555 B2 * | 1/2015 | Tremper | ............. | A61B 5/02 |
| | | | | 600/595 |
| 8,959,781 B2 * | 2/2015 | Delort | ............. | G02C 13/005 |
| | | | | 33/200 |
| 9,307,930 B2 * | 4/2016 | Todd | ............. | A61B 5/1075 |
| 10,029,061 B2 * | 7/2018 | Grashow | ............. | A61B 5/1077 |
| 10,080,528 B2 * | 9/2018 | DeBusschere | ......... | A61B 5/742 |
| 10,314,996 B2 * | 6/2019 | Tang Ee Ho | ........ | A61B 5/1072 |
| 10,709,358 B2 * | 7/2020 | Aarestad | ............. | A61B 5/4851 |
| 10,835,359 B2 * | 11/2020 | Wagner | ............. | A61B 3/111 |
| 2003/0221327 A1 * | 12/2003 | Bonzagni | ............. | B65D 75/32 |
| | | | | 33/512 |
| 2006/0090362 A1 * | 5/2006 | Wood | ............. | A61B 5/107 |
| | | | | 33/512 |
| 2006/0281978 A1 * | 12/2006 | Crucilla | ............. | A61B 5/681 |
| | | | | 600/595 |
| 2007/0209219 A1 * | 9/2007 | Ertmer | ............. | A01K 97/00 |
| | | | | 33/511 |
| 2014/0220520 A1 * | 8/2014 | Salamini | ............. | A61B 5/7455 |
| | | | | 434/185 |
| 2016/0038032 A1 | 2/2016 | Dan | | |
| 2016/0278670 A1 | 9/2016 | Schoettker et al. | | |
| 2017/0296315 A1 * | 10/2017 | Bakeman | ............. | A61B 5/1072 |
| 2017/0337338 A1 | 11/2017 | Dunn et al. | | |
| 2018/0214070 A1 * | 8/2018 | McDaniel | ............. | A61B 5/444 |
| 2020/0135310 A1 * | 4/2020 | Gedamu | ............. | A61B 5/0022 |
| 2023/0044289 A1 * | 2/2023 | Jiang | ............. | G10L 25/90 |
| 2023/0124570 A1 * | 4/2023 | Spencer | ............. | A61B 5/7455 |
| | | | | 600/590 |
| 2024/0008732 A1 * | 1/2024 | Huang | ............. | A61B 1/00052 |

OTHER PUBLICATIONS

"Difficult Airway Algorithm," Quizlet.com. https://quizlet.com/207761444/difficult-airway-algorithm-flash-cards/ [Date accessed: Oct. 23, 2020].

"Airway Pearls: Assessing Airway Difficulty," iem-student.org. https://iem-student.org/2018/08/01/assessing-airway-difficulty-lemon/ [Date accessed: Oct. 23, 2020].

"EMS Difficult Airway Algorithm," theairwaystore.com. https://the-airway-store.myshopify.com/products/the-airway-card-ems-v4-5 [Date accessed: Oct. 23, 2020].

* cited by examiner

PRE-OPERATIVE ASSESSMENT TOOL AND METHOD FOR PREDICTING DIFFICULT AIRWAY

CROSS-REFERENCE TO RELATED APPLICATIONS

This application is a non-provisional application which claims priority to U.S. Provisional Patent Application No. 63/164,182 filed on Mar. 22, 2021, which is incorporated by reference in its entirety.

FIELD OF DISCLOSURE

The invention is directed to systems and methods for assessing anatomical structures as part of a pre-operative assessment of a subject, and more specifically to assessing anatomical structures relevant for predicting difficult mask ventilation and difficult intubation.

BACKGROUND

Pre-operative assessment of the airway is an essential step in ensuring the safety and positive outcomes of a subject undergoing surgery. The purpose of the assessment is to predict potential problems to allow a management plan to be developed ahead of time and thus avoid a catastrophe due to unanticipated difficult airway. In doing an assessment, the goal is to plan ahead for potential problems in two areas: 1) laryngoscopy and intubation, and 2) ventilation. Accordingly, patients are subject to a pre-operation airway examination looking for anatomical features that are potentially indicative of difficulty in ventilation or intubation.

In anesthesia practice, direct laryngoscopy is a procedure used to visualize the larynx in order to place an endotracheal tube. The procedure requires adequate mouth opening and proper positioning, entailing cervical flexion and atlanto-occipital extension. Most predictive tests check one or more of these capabilities to make an assessment. Mask ventilation requires a face mask producing an effective seal around the mouth and nose and an open airway. There are certain anatomical and physical features which provide a guideline to predict difficult mask ventilation. Prior to sedation or anesthesia, an evaluation is made for potential difficulties in mask ventilation and/or endotracheal intubation which may include some of the predictive tests, and physical and anatomical feature examination. However, there does not seem to be a universally recognized method to predict difficult airway for intubation or mask ventilation.

Accordingly, there is still an unsolved need for a structured approach for evaluating and making a more accurate and confident prediction on difficult airway as part of a pre-operative assessment that may address these and other existing issues.

SUMMARY

According to one embodiment, one or more embodiments are provided below for a system and method for predicting a difficult airway for intubation or mask ventilation that provides a structured approach to evaluating and correlating predictive tests and anatomic features in making a more accurate and confident prediction on difficult airway.

The system may be provided as a two-sided card wherein a first side of the card may include a combination of predictive tests that are shown to be the most helpful in predicting a difficult airway. A ruler is also provided on an edge of the card to assist with measurements, along with an inch to centimeter conversion factor. A second side of the card includes a list of contributing factors for a difficult airway and clinical assessments findings associated with difficult mask ventilation. This cognitive aid may also comprise of a method to use the combination of predictive tests and contributing factors in conducting a thorough and confident assessment of an airway prior to a surgical procedure requiring anesthesia.

Other aspects and advantages of the invention will be apparent from the following description and the appended claims.

BRIEF DESCRIPTION OF THE FIGURES

Embodiments of the present disclosure are described in detail below with reference to the following drawings. These and other features, aspects, and advantages of the present disclosure will become better understood with regard to the following description, appended claims, and accompanying drawings. The drawings described herein are for illustrative purposes only of selected embodiments and not all possible implementations and are not intended to limit the scope of the present disclosure.

DETAILED DESCRIPTION

Figure 1A:
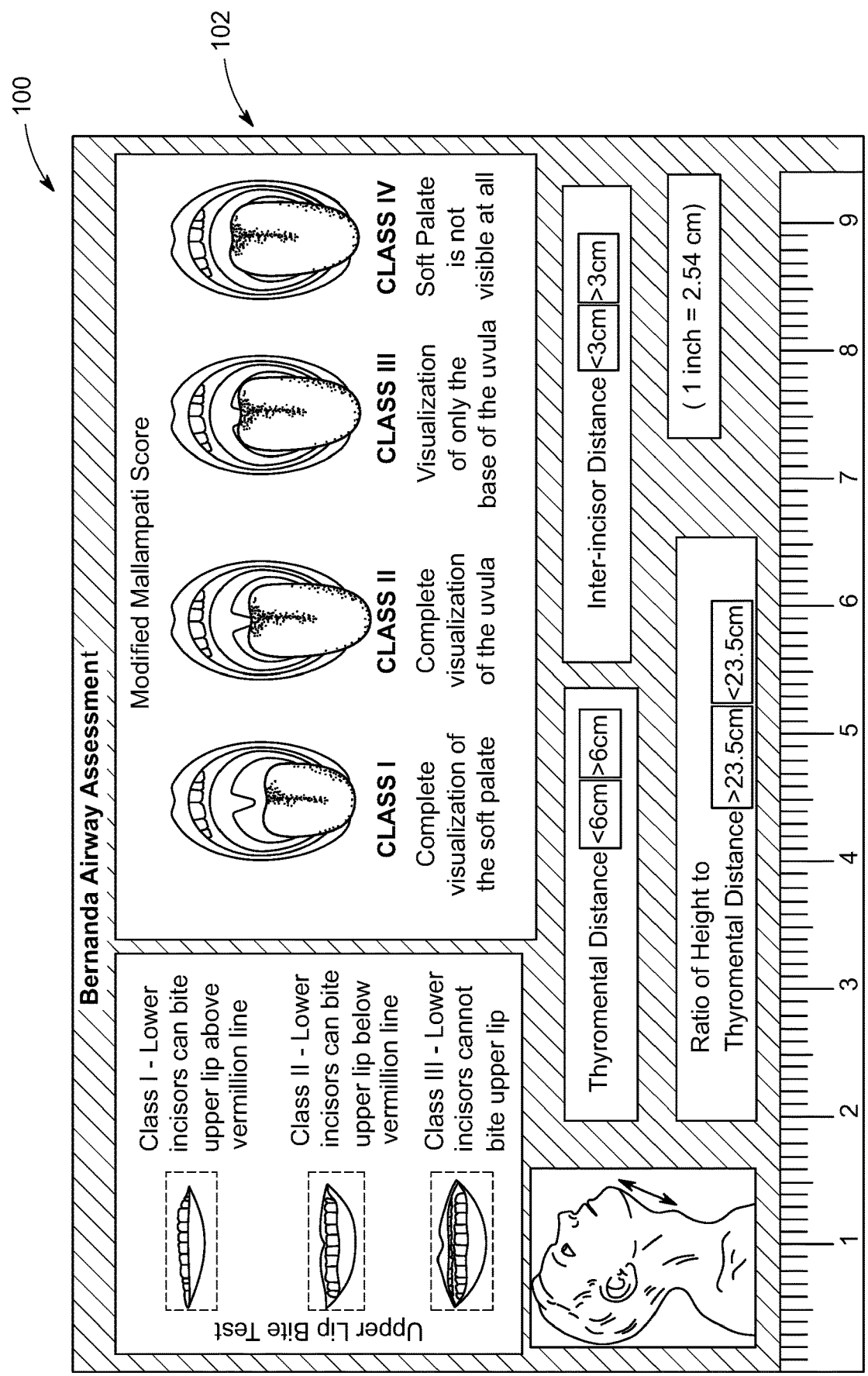
FIG. 1A shows an exemplary embodiment of a first side of an airway assessment card listing predictive tests.

In the Summary above and in this Detailed Description, and the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature may also be used, to the extent possible, in combination with and/or in the context of other particular aspects and embodiments of the invention, and in the invention generally.

Where reference is made herein to a method comprising two or more defined steps, the defined steps may be carried out in any order or simultaneously (except where the context excludes that possibility), and the method may include one or more other steps which are carried out before any of the defined steps, between two of the defined steps, or after all the defined steps (except where the context excludes that possibility).

"Exemplary" is used herein to mean "serving as an example, instance, or illustration." Any aspect described in this document as "exemplary" is not necessarily to be construed as preferred or advantageous over other aspects.

Throughout the drawings, like reference characters are used to designate like elements. As used herein, the term "coupled" or "coupling" may indicate a connection. The connection may be a direct or an indirect connection between one or more items. Further, the term "set" as used herein may denote one or more of any item(s), so a "set of items" may indicate the presence of only one item or may indicate more items. Thus, the term "set" may be equivalent to "one or more" as used herein.

The present disclosure recognizes a need for a more universal system and method for predicting a difficult airway for intubation or mask ventilation. The present disclosure provides for a combination of predictive tests and their values that are shown to be the most accurate in evaluating difficult airways. The present disclosure also provides a cognitive aid to assess for contributing factors for difficult airways. The present disclosure also provides for a system and method to assist the healthcare provider in performing the included airway assessments accurately. The present disclosure provides for the predictive tests and the contributing factors as a system that is readily available on a person making the assessment.

The present disclosure includes a system and method of a pre-operative evaluation and assessment to properly make a prediction of the level of difficult airway and select the most appropriate method of intubation or breathing assistance for a patient. The system may be provided as a two-sided card and referred to as an airway assessment card which may be carried on a person (i.e., clinician) at all times and thus be readily available to make an assessment. One side of the card may include a combination of predictive tests that are shown to be the most helpful in predicting a difficult airway. Predictive tests on the card comprise of at least: Thyromental Distance, Mallampati Score, Upper Lip Bite Test, Ratio of Height to Thyromental Distance, & Inter-Incisor Distance. A ruler is also provided on an edge of the card to assist with measurements, along with an inch to centimeter conversion factor. On the other side of the card is provided a list of contributing factors for a difficult airway and clinical assessments findings associated with difficult mask ventilation. The cognitive aid may also comprise of a method to use the combination of predictive tests and contributing factors in conducting a thorough and confident assessment of an airway prior to a surgical procedure requiring anesthesia.

Use of the airway assessment card using the method described herein has several advantages including, and not limited to, serving as a reminder to perform the airway assessment, assisting the healthcare provider in performing the airway assessment accurately with the listed criteria and their values, building confidence in making the airway assessment, readily and conveniently available on a person to ensure the assessment is made correctly, and combining tests that are shown to be the most predictive in assessing an airway of a subject.

The presently disclosed airway assessment card and method of use are more fully described in conjunction with the figures.

Figure 1B:
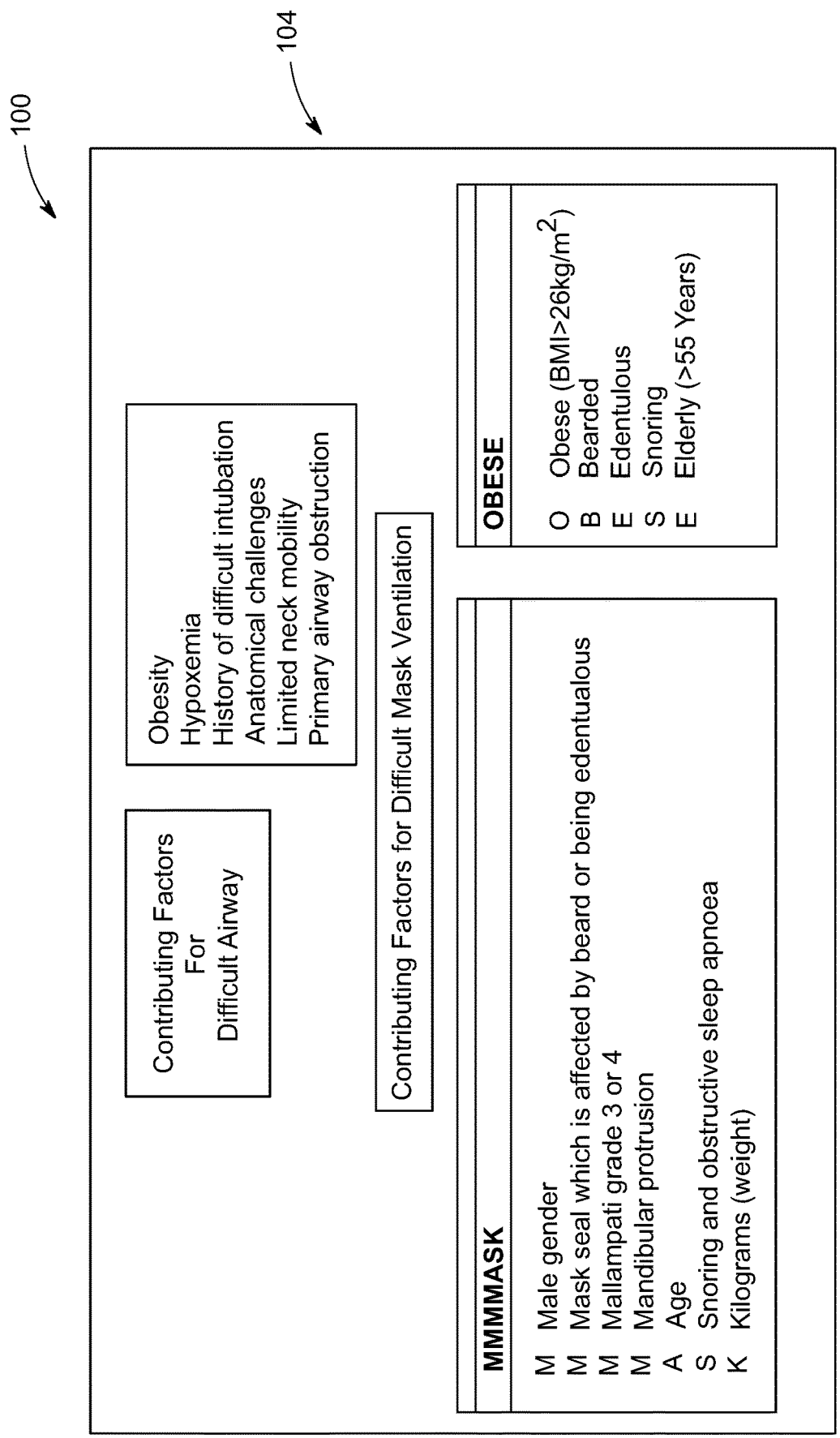
FIG. 1B an exemplary embodiment of a second side of an airway assessment card listing contributing factors.

In the non-limiting embodiment as shown in FIGS. 1A and 1B, an airway assessment card 100 is provided. The airway assessment card 100 as disclosed herein may generally be a two-sided card designed to accommodate predictive tests to assess an airway and contributing factors that may lead to difficult intubation, ventilation, or extubation. FIG. 1A shows a first side of the airway assessment card 100, referred to as the predictive test side 102 herein, which may be comprised of several predictive tests used in a physical examination of an airway. FIG. 1B shows a second side of the airway assessment card 100, referred to as contributing factors side 104, which may comprise of factors that may contribute to a difficult intubation, ventilation, or extubation. The airway assessment card 100 is a physical card that is designed to be carried on a person so that it is readily available to use. The airway assessment card 100 may be fashioned from material that is durable so that it can withstand repetitive use. Additionally, the airway assessment card may be provided with a plastic sleeve.

Referring to FIG. 1A, the predictive test side 102 is comprised of several tests which were determined through literature research to be the most accurate in predicting a difficult airway. The listed predictive tests comprise of Thyromental Distance, Mallampati Score, Upper Lip Bite Test, Ratio of Height to Thyromental Distance, and Inter-Incisor Distance. The predictive test side 102 also lists the appropriate scoring for each predictive test. Other predictive tests and their appropriate scoring that may be deemed important or may be deemed important in the future can also comprise part of the predictive tests listed on the predictive test side 102. Additionally, a ruler is also designed along an edge of the airway assessment card 100, which may be included on the predictive test side 102, the contributing factors side 104, or on both sides. The ruler may be provided in inches with up to 9 inches of reading. Additionally, a conversion scale of inches to centimeters is also provided for quick reference. The provider making the assessment can convert the measured distance from inches to centimeters or vice versa to determine which range the measurement of the anatomical features falls into, a safe zone indicated by a green color or an unsafe zone determined by a red color.

Referring to FIG. 1B, the contributing factors side 104 is comprised of factors for a healthcare provider to consider and ask a patient when making an assessment of the physical characteristic and non-physical characteristics that can lead to a difficult airway. The contributing factors side 104 may be comprised of contributing factors for difficult airway and contributing factors for difficult mask ventilation. Other factors that may be deemed important or may be deemed important in the future may also comprise part of the factors listed on the contributing factors side 104.

In the example shown in FIG. 1B, the contributing factors for a difficult airway include obesity, hypoxemia, history of difficult intubation anatomical challenges, limited neck mobility, and primary airway obstruction. The contributing factors for difficult mark ventilation include the acronyms "MMMMASK" and "OBESE." The "MMMMASK" acronym includes male gender, mask seal which is affected by beard or being edentulous, Mallampati grade 3 or 4, mandibular protrusion, age, snoring and obstructive sleep apnoea, and kilograms (weight). The "OBESE" acronym includes obese, bearded, edentulous, snoring, and elderly.

Figure 2:
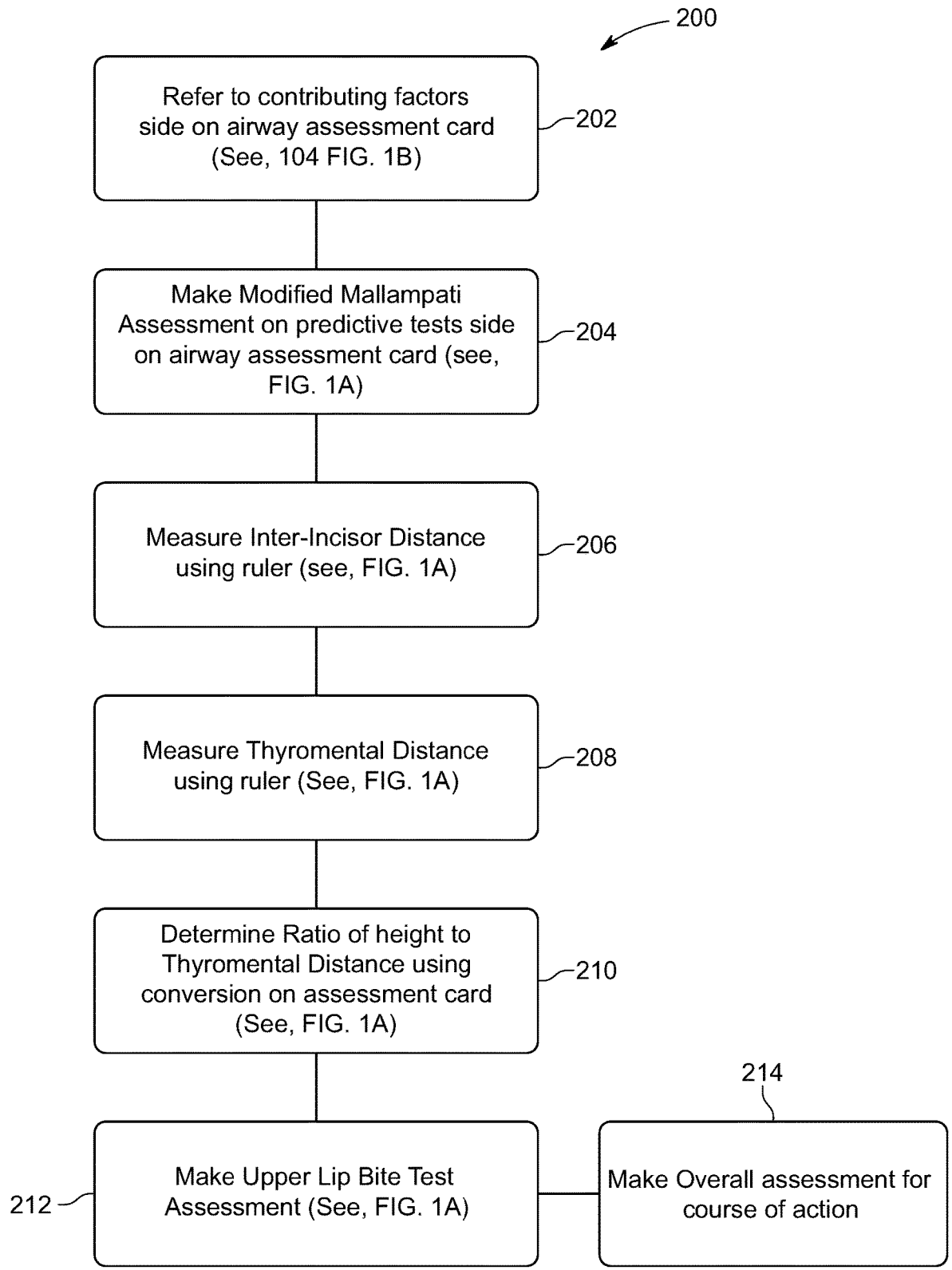
FIG. 2 is a flowchart of a method of making a pre-operative assessment using the airway assessment card in accordance with an illustrative embodiment.

FIG. 2 refers to a method or steps that may be taken to make a pre-operative assessment of a difficult intubation or ventilation of a subject, which may be made using the airway assessment card 100 discussed above. In one embodiment, as shown in FIG. 2, the airway assessment card 100 is referred to in order to start making a pre-operative assessment. The assessment may be started by referring to the contributing factors side 104 (See, FIG. 1B) of the airway assessment card 100 and identify those factors (at 202). In this step, with the aid of the airway assessment card (see, FIG. 1B) the provider is assessing for physical characteristics included on the card as well as asking the specific questions of a patient that are not visible during physical assessment and looking at their health history.

Next (at 204), the assessment moves to the predictive tests side 102 (see, FIG. 1A) and starts with the Modified Mallampati Assessment. The healthcare provider refers to the illustrations with the appropriate scoring on the airway assessment card 100 in FIG. 1A.

Then (at 206), the healthcare provider measures the Inter-Incisor Distance. In making the measurement, the ruler, as shown in FIG. 1A, on the airway assessment card 100 can be used. The difficulty can be assessed and determined with the color-coded measurement ranges provided on the airway assessment. As shown in FIG. 1A, the red color and green color make it visually clear as to the measurements that may provide some difficulty for intubation.

Then (at 208), the Thyromental Distance is measured with the ruler provided on the airway assessment card 100 in FIG. 1A. The airway assessment card 100 also provides an illustration to show how to make the correct measurement. Additionally, a color-coded numerical range is provided to readily show which range would contribute to difficulty in red and which range would likely not contribute to difficulty in green.

Next (at 210), the Thyromental Distance measurement can be used in determining the Ratio of Height to Thyromental Distance. An inch to centimeter conversion is also provided on the airway assessment card 100, as shown in FIG. 1A. At this step, the conversion of a patient's height from inches to centimeters is made and is generally considered necessary to determine the ratio. The color-coded numerical values in red and green are provided indicating difficult and unlikely difficult airway, respectively.

Then (at 212), the Upper Lip Bite Test assessment is made by assessing the subject's lips by having the subject bite the upper lip with the lower incisors. The illustration on the airway assessment card 100 in FIG. 1A can be referenced to determine the accurate class of the assessment.

Closing out FIG. 2 (at 214), the overall assessment leads to determining the course of action or a plan for the surgical procedure requiring intubation or mask ventilation.

The steps listed herein and comprising a part of the present disclosure may be included as an additional insert, such as a card, to be included with the airway assessment card 100.

This method results in a detailed assessment of a patient's airway prior to performing a surgery. The predictive tests and the contributing factors listed on the airway assessment card 100 provide for a step-by-step assessment which ensures that the necessary tests and examination have been made. The illustrations and numerical values also provide a convenient and readily accessible means to make a confident assessment. The airway assessment card ensures that the predictive tests and contributing factors are always performed and that these are readily available on a person. In most circumstances, healthcare providers or other healthcare professional doing a pre-operative assessment of the airway, perform these assessments and tests from memory and may not perform an appropriate number of tests and consider all the contributing factors that provide a more accurate assessment of a subject's airway. The result being that the assessment may not be the most accurate and confident. The predictive tests and contributing factors listed on the assessment card are included to ensure that these are readily available on a healthcare professional doing the assessment and the appropriate ranges are provided to make a confident overall analysis.

It is understood that the acts described above are meant as a general overview and demonstration of an exemplary method, and that the method may include different and/or additional acts as described herein or otherwise.

While the present invention has been described as having particular configurations disclosed herein, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention.

The embodiments were chosen and described in order to best explain the principles of the invention and the practical application, and to enable others of ordinary skill in the art to understand the invention for various embodiments with various modifications as are suited to the particular use contemplated. The present invention according to one or more embodiments described in the present description may be practiced with modification and alteration within the spirit and scope of the appended claims. Thus, the description is to be regarded as illustrative instead of restrictive of the present invention.

What is claimed is:

1. A cognitive aid, comprising:
 a card having two sides, a first side and a second side, wherein:
  the first side is referred to as a predictive test side, comprising a summary of predictive tests to be used in determining difficulty in intubation;
  the second side is referred to as a contributing factors side, comprising contributing factors for difficult airway and contributing factors for difficult mask ventilation;
 a ruler configured along an edge of the card; and
 wherein, the card is a pre-operative aid for assessing difficulty in intubation or ventilation of a subject.

2. The cognitive aid of claim 1, wherein the first side lists appropriate scoring for each of the predictive tests.

3. The cognitive aid of claim 1, wherein the predictive tests comprise of Thyromental Distance, Mallampati Score, Upper Lip Bite Test, Ratio of Height to Thyromental Distance, and Inter-Incisor Distance.

4. The cognitive aid of claim 3, wherein the appropriate scoring of each of the predictive tests is listed on the first side.

5. The cognitive aid of claim 1, wherein the second side comprising contributing factors for difficult airway and difficult mask ventilation are provided as an acronym.

6. The cognitive aid of claim 1, wherein the contributing factors for difficult airway provided on the second side of the card include male gender, mask seal affected by beard or being edentulous, Mallampati grade 3 or 4, mandibular protrusion, age, snoring and obstructive sleep apnoea, and weight in kilograms, and
 wherein the contributing factors for difficult mask ventilation provided on the second side of the card include obese, bearded, edentulous, snoring, and elderly.

7. The cognitive aid of claim 1, wherein the ruler is included along an edge of the card on the first side or the second side.

8. The cognitive aid of claim 7, wherein the ruler is provided in inches and a conversion scale from inches to centimeters is included on the card.

9. The cognitive aid of claim 1, wherein the card is provided with a plastic sleeve.

10. The cognitive aid of claim 1, wherein the card is carried on a person.

11. A pre-operative method of assessing difficulty in intubation and/or ventilation of a subject using a cognitive aid, comprising:
  assessing a plurality of contributing factors by referring to a contributing factors side on the cognitive aid;
  assessing difficulty in intubation by referring to a predictive tests side on the cognitive aid;
  referring to the color-coded numerical ranges on the cognitive aid in determining whether any of the contributing factors or the predictive tests are likely to contribute to difficulty in intubation and/or ventilation; and
  determining a plan for intubation and/or ventilation based on the contributing factors and predictive tests assessment.

12. The method of claim 11, wherein assessing the contributing factors by looking at the physical characteristics of the subject listed on the cognitive aid, asking questions of the subject, and referencing the health history of the subject.

13. The method of claim 11, wherein scoring a Modified Mallampati score by referring to an illustration with the appropriate scoring on the cognitive aid as part of the predictive test.

14. The method of claim 11, wherein measuring an inter-incisor distance by using a ruler included on the cognitive aid and referring to the illustration showing how to make a correct measurement as part of the predictive test and referring to the color-coded numerical ranges.

15. The method of claim 11, wherein measuring a thyromental distance by using a ruler included on the cognitive aid and referring to the illustration showing how to make a correct measurement as part of the predictive test and referring to the color-coded numerical ranges.

16. The method of claim 15, further determining a ratio of the subject's height to thyromental distance by converting the subject's height from inches to centimeters by using an inch to centimeter conversion scale provided on the cognitive aid, wherein assessing the ratio calculated in centimeters by referring to the color-coded numerical ranges as part of the predictive test.

17. The method of claim 11, wherein assessing the lower incisors and lips of the subject by conducting the upper lip bite test by referring to an illustration showing each class of the upper lip bite test as part of the predictive test.

18. The method of claim 11, wherein determining a course of action for a surgical procedure based on an overall assessment of all the contributing factors and the predictive tests listed on the cognitive aid.

* * * * *